United States Patent
Wismeijer

(10) Patent No.: US 11,839,525 B2
(45) Date of Patent: Dec. 12, 2023

(54) CUSTOMIZED DENTAL IMPLANT AND ASSOCIATED TOOLING

(71) Applicant: Stichting VU, Amsterdam (NL)

(72) Inventor: Daniel Wismeijer, Amsterdam (NL)

(73) Assignee: STICHTING VU

( * ) Notice: Subject to any disclaimer, the term of this patent is extended or adjusted under 35 U.S.C. 154(b) by 445 days.

(21) Appl. No.: 15/572,617

(22) PCT Filed: May 4, 2016

(86) PCT No.: PCT/EP2016/059980
§ 371 (c)(1),
(2) Date: Nov. 8, 2017

(87) PCT Pub. No.: WO2016/180700
PCT Pub. Date: Nov. 17, 2016

(65) Prior Publication Data
US 2018/0140392 A1 May 24, 2018

(30) Foreign Application Priority Data
May 8, 2015 (EP) .................................... 15167007

(51) Int. Cl.
*A61C 8/00* (2006.01)
*A61C 13/00* (2006.01)
(Continued)

(52) U.S. Cl.
CPC ............ *A61C 8/0089* (2013.01); *A61B 5/055* (2013.01); *A61B 6/032* (2013.01); *A61C 1/084* (2013.01);
(Continued)

(58) Field of Classification Search
CPC ... A61C 8/0089; A61C 13/0004; A61B 1/001; A61B 2034/108; A61B 2034/102
See application file for complete search history.

(56) References Cited

U.S. PATENT DOCUMENTS 5,967,777 A * 10/1999 Klein .................. A61C 8/0089
433/75
6,039,568 A * 3/2000 Hinds .................. A61C 8/0036
433/175

(Continued)

FOREIGN PATENT DOCUMENTS

| WO | 2006031096 A1 | 3/2006 |
| WO | 2012004937 A1 | 1/2012 |

OTHER PUBLICATIONS

International Search Report dated Jul. 15, 2016 for corresponding International Application PCT/EP2016/059980, filed May 4, 2016.
(Continued)

*Primary Examiner* — Ralph A Lewis
(74) *Attorney, Agent, or Firm* — Mendelsohn Dunleavy, P.C.

(57) ABSTRACT

Method of customizing and manufacturing tooling for preparing an osteotomy for receiving a dental implant, in particular drills and/or osteotomes. The method comprises the steps of: —receiving scan data modeling a planned position of the osteotomy and surrounding jaw bone area; —generating on the basis of the scan data a virtual implant model of the dental implant; —generating a virtual tooling model of the tooling on basis of the virtual implant model; —computer aided manufacturing of the tooling on the basis of the virtual tooling model.

16 Claims, 2 Drawing Sheets

(51) Int. Cl.
*A61C 1/08* (2006.01)
*A61C 3/02* (2006.01)
*B33Y 50/00* (2015.01)
*B33Y 80/00* (2015.01)
*A61B 5/055* (2006.01)
*A61B 6/03* (2006.01)
*A61C 9/00* (2006.01)
*G16H 20/40* (2018.01)
*B28B 1/00* (2006.01)

(52) U.S. Cl.
CPC .............. *A61C 3/02* (2013.01); *A61C 9/004* (2013.01); *A61C 13/0004* (2013.01); *B33Y 50/00* (2014.12); *B33Y 80/00* (2014.12); *B28B 1/001* (2013.01); *G16H 20/40* (2018.01)

(56) References Cited

U.S. PATENT DOCUMENTS

| | | | | |
|---|---|---|---|---|
| 8,414,296 | B2* | 4/2013 | Berckmans, III | A61C 1/084 433/215 |
| 8,738,165 | B2* | 5/2014 | Cinader, Jr. | B33Y 50/00 433/24 |
| 9,060,832 | B2* | 6/2015 | Karim | A61C 13/0009 |
| 2006/0093988 | A1* | 5/2006 | Swaelens | A61C 1/084 433/76 |
| 2006/0223029 | A1* | 10/2006 | Berger | A61C 13/275 433/172 |
| 2008/0085489 | A1* | 4/2008 | Schmitt | A61C 1/084 433/75 |
| 2008/0228303 | A1* | 9/2008 | Schmitt | G05B 19/4097 700/98 |
| 2009/0042167 | A1* | 2/2009 | Van Der Zel | A61C 8/0069 433/215 |
| 2009/0248184 | A1* | 10/2009 | Steingart | A61C 1/082 700/98 |
| 2009/0263764 | A1* | 10/2009 | Berckmans, III | A61C 8/0089 433/215 |
| 2010/0233647 | A1* | 9/2010 | Yang | A61C 1/084 433/66 |
| 2011/0066267 | A1* | 3/2011 | Schmitt | A61C 1/084 700/98 |
| 2011/0136077 | A1* | 6/2011 | De Moyer | A61C 13/0004 433/173 |
| 2011/0269104 | A1 | 11/2011 | Berckmans, III et al. | |
| 2012/0046668 | A1* | 2/2012 | Gantes | A61C 1/084 606/130 |
| 2012/0323546 | A1* | 12/2012 | Berckmans, III | A61C 1/084 703/11 |
| 2013/0209960 | A1* | 8/2013 | Benhamou | A61C 8/0075 433/174 |
| 2013/0230827 | A1* | 9/2013 | Kwon | A61C 3/02 433/183 |
| 2013/0244205 | A1 | 9/2013 | Berckmans, III et al. | |
| 2013/0244206 | A1* | 9/2013 | Bullis | A61C 8/0089 433/173 |
| 2014/0038134 | A1* | 2/2014 | Nguyen | A61C 8/0089 433/175 |
| 2014/0172111 | A1* | 6/2014 | Lang | A61F 2/461 623/20.32 |
| 2014/0212843 | A1* | 7/2014 | Chiu | A61K 6/84 433/201.1 |
| 2014/0272790 | A1 | 9/2014 | Aerni | |
| 2015/0037756 | A1 | 2/2015 | Berckmans, III et al. | |
| 2015/0250557 | A1* | 9/2015 | Simmons, Jr. | A61C 1/084 433/118 |
| 2015/0265373 | A1* | 9/2015 | Jamison | A61C 1/085 433/173 |
| 2015/0351866 | A1* | 12/2015 | Thompson, Jr. | A61C 1/084 433/173 |
| 2015/0366635 | A1* | 12/2015 | Shotton | A61C 5/42 433/102 |

OTHER PUBLICATIONS

Written Opinion of the International Searching Authority dated Nov. 17, 2016 for corresponding International Application PCT/EP2016/059980, filed May 4, 2016.
Communication pursuant to Article 94(3) EPC for corresponding European application No. 16721779.3; dated Apr. 20, 2020 (6 pages).
Notice of Reasons for Rejection for corresponding Japanese application No. 2018-609982; dated May 11, 2021 (10 pages).
Ireland Robert, "A Dictionary of Dentistry." Oxford University Press Inc., New York. (2010): p. 255.
Younes, Ronald, et al. "Sinus Grafting Techniques: A Step-by-Step Guide." Springer International Publishing, New York. (2015): p. 107.

* cited by examiner

CUSTOMIZED DENTAL IMPLANT AND ASSOCIATED TOOLING

FIELD OF THE INVENTION

The present invention relates to a method of customizing and manufacturing a dental implant and associated tooling for implanting the dental implant. The invention also relates to the tooling and to a set of the tooling and an implant customized and manufactured by the method.

BACKGROUND OF THE INVENTION

A dental implant is an endosseous surgical implant that serves to replace the root of a lost tooth and that interfaces with a bone of a patient's jaw to support a dental prosthesis such as a crown, bridge, denture, facial prosthesis or to act as an orthodontic anchor. Such a dental implant, usually a cylindrical or slightly conical component, is typically inserted or screwed into a drilled hole or osteotomy in the jawbone. Dental implants are made of a bio-compatible material, such as titanium or zirconia, and bond to adjacent bone material by osseointegration.

Before placing the dental implants their position should be carefully planned taking into account the shape, size, and position of the jaw bones and adjacent and opposing teeth. A dentist may use a CT scan of the jawbone and plan the surgery using computer software. The use of CT scanning in complex cases also enables identifying and avoiding vital structures such as the inferior alveolar nerve in the lower jaw and the maxillary sinus in the upper jaw.

A sufficient body of jaw bone should be maintained between the implant and adjacent denture to ensure a proper blood supply. To this end, a minimum distance of 1.5 to 2 millimeters is usually maintained between the implant and the adjacent teeth on either side of the implant and 1.5 to 3 millimeters between adjacent multiple implants. This means that the available bone site for placement of a dental implant is limited and requires the surgeon to exercise considerable care.

Generally, the implant is placed a number of months after removal of the lost tooth, in order to allow recovery of the hole left by the root of the lost tooth, the so-called dental alveolus. Alternatively, the implant can be placed before complete healing, when the dental alveolus is still present.

To place a dental implant an incision is often made first to expose the jaw's bone. The surgeon can then use a tailor made drill guide or stent for optimal positioning and guiding of the drills to be used. WO 2006/031096 discloses that such a drill guide can be made by stereolithography or rapid prototyping om basis of a CT scan. Pilot holes are placed with precision drills at highly regulated speed to prevent burning or pressure necrosis of the bone. The pilot hole is then expanded by consecutive use of drills with increasingly larger diameters. Usually, between about three to seven drilling steps are carried out. The drills to be used are available in a limited number of standardized diameters, lengths and conical angles.

When the desired hole is drilled, the implant screw is placed. The implant may for instance be a self-tapping screw.

It is an object of the invention to enable optimum use of the present bone material and the available space for positioning an implant.

SUMMARY OF THE INVENTION

The object of the invention is achieved with a method of customizing and manufacturing a dental implant and tooling for preparing an osteotomy for receiving the dental implant, the method comprising the steps of:

receiving scan data modeling a jaw bone area comprising a planned position of the osteotomy;

generating on basis of the scan data a virtual implant model of the dental implant;

generating a virtual tooling model of the tooling on basis of the virtual implant model;

computer aided manufacturing of the tooling on basis of the virtual tooling model.

Customizing the tooling, and preferably also the implant design, makes it possible to make maximum use of the space and bone material available for osseointegration of the implant. Moreover, the on-demand availability of toolings of any desired type and size contributes substantially to procedural efficiency.

In particular the drills can be customized this way. Instead of being dependent on a limited number of standardized drills, the drill diameter, drill length and optionally a conical angle can be customized and optimized for the specific situation and the individual implant design. Other dental osteotomy modeling devices can also be customized this way, such as scrapers, cutters, chisels, etc.

Where in prior art systems scan data and 3D printing are typically used for implants or prostheses, requiring an accurate match and fit, the present invention makes it possible to translate scan data to tailor-made and on-demand manufacturable drills and/or other osteotomes.

Also the dental implant can be made by a computer aided manufacturing process on the basis of said virtual implant model.

In exceptional cases, the dental implant can be an existing tooth, e.g., a tooth that is transplanted from one part of a patients' jaw to another part. In such a case, the scan data include scan data of the tooth to be transplanted. These scan data are the basis of the virtual implant model.

The scan data model at least the section of the jaw bone comprising the alveolus and adjacent dentures.

The scan data can for example be obtained by a computed tomography (CT) scan. Other scanning technologies, include but are not limited to CBCT, MRT, MRI, PET, SPECT, ultra sound, destructive scanning, active triangulation, passive triangulation, confocal scanning, and TOF (Time Of Flight). Combinations of scans can also be used. For instance, CT-scans can be used for modeling the local anatomy of the harder tissues, such as local jaw bone tissue, while an MRI scan can be used for modeling softer tissues, such as nerves. CT-scans may for example also be combined with intraoral scans.

Scan methods are generating either surface descriptions for example in STL-format or volumetric data for example in a so called "voxel"-format that can be transformed into surface data by generally available software applications.

The scan data are used to produce a computer generated virtual implant model of the dental implant. The implant can be designed to make optimum use of available space and bone material. A suitable example of a process of generating a virtual implant model is disclosed in WO 2006/031096. The model includes geometrical information of the dental implant and positioning data defining the exact position and orientation of the dental implant in the jaw bone.

The design of the generated implant model may have any suitable shape or diameter at any level of the implant, the implant being wider at the top and narrower at the lowest point.

Additionally, a virtual model of a drill guide can be generated on basis of the virtual implant model. The drill guide is adapted to the shape and size of the implant. A suitable example of a process of generating a virtual drill guide model on basis of CT-scan data is also disclosed in WO 2006/031096.

Knowing the dimensions of the designed implant, the required drills can be designed. The drills can be designed for preparing a hole providing a tight fit for the implant in order to provide initial stability of the implant just after positioning.

Since the drills are manufactured individually they do not need to have a standard diameter. Design parameters that can be derived from the virtual implant model include the diameter, the length and optionally a conical angle or pitch. The virtual tooling model for the drills may be based on a generic virtual tooling model to be completed by open design parameters, in particular diameter and length.

After generation of the virtual models of the implant, the toolings and optionally the drill guide, the respective products can be manufactured by a computer aided process, e.g., a rapid prototyping process allowing on-demand precise manufacture of the desired products. Suitable rapid prototyping process include stereolithography, fused deposition modeling, laminated object modeling, selective laser sintering, computer aided milling and, in particular, 3D printing. Combinations can also be used. For instance, a slightly oversized product may be printed and subsequently milled to improve dimensional accuracy or to obtain a desired surface finishing.

Notwithstanding the geometrical diversity of the products, the same rapid typing process, device and/or materials can be used to manufacture the implant, the toolings and, optionally, the drilling guide. With a single 3D printer the surgeon may print all the elements he needs with the preparation for a treatment. Furthermore, use of a 3D printer allows the surgeon to use different materials for specific layer. For instance, the implant may be provided with a top surface with a material stimulating growth of bone material. For instance, apatite coated zirconia was found to promote adherence to jaw bone material. The drill surfaces may for example be provided with hemostyptics or materials promoting healing of the drilled tissues.

Examples of printing materials include, but are not limited to, ceramics based on zirconia, apatite, ytrria, hafnia, alumina, ceria, magnesia, titania, silicon nitride, silicon carbide, silica-alumina-nitride, mullite, garnets, porcelain, or mixtures thereof. In particular zirconia based materials show good biocompatible properties.

An example of a suitable 3D printer is the Objet Eden260VTM 3D Printer, commercially available from Stratasys Ltd.

After use the toolings can be disposed. Optionally, the printing material can be recycled.

The invention also relates to a set of the aforementioned toolings for preparing implantation of a dental implant.

Such a set of toolings may for example include a drill comprising a guiding section and a drilling guide comprising a guiding opening configured to receive the guiding section of the drill in a sliding manner. This allows accurate positioning and directing of the drill. The guiding section may for instance be a collar, e.g., a cylindrical collar, the drill guide having an opening of a matching diameter.

The set may for instance comprise a series of drills of increasing diameter, all provided with a guiding section of the same dimensions. As a result all drills of the series can be accurately guided by the drill guide.

Optionally, the guiding section of the drill or the matching guiding opening in the drill guide may comprise a stop to prevent that the drill may be moved to deep. The exact position of the stop can be part of the virtual tooling model derived from the scan data.

The set may also comprise a customized dental implant, e.g., printed with the same 3D printer or other rapid prototyping station as the toolings, optionally of the same printing material.

The invention will be further explained with reference to the accompanying drawings, showing exemplary embodiments.

DETAILED DESCRIPTION

Figure 1:
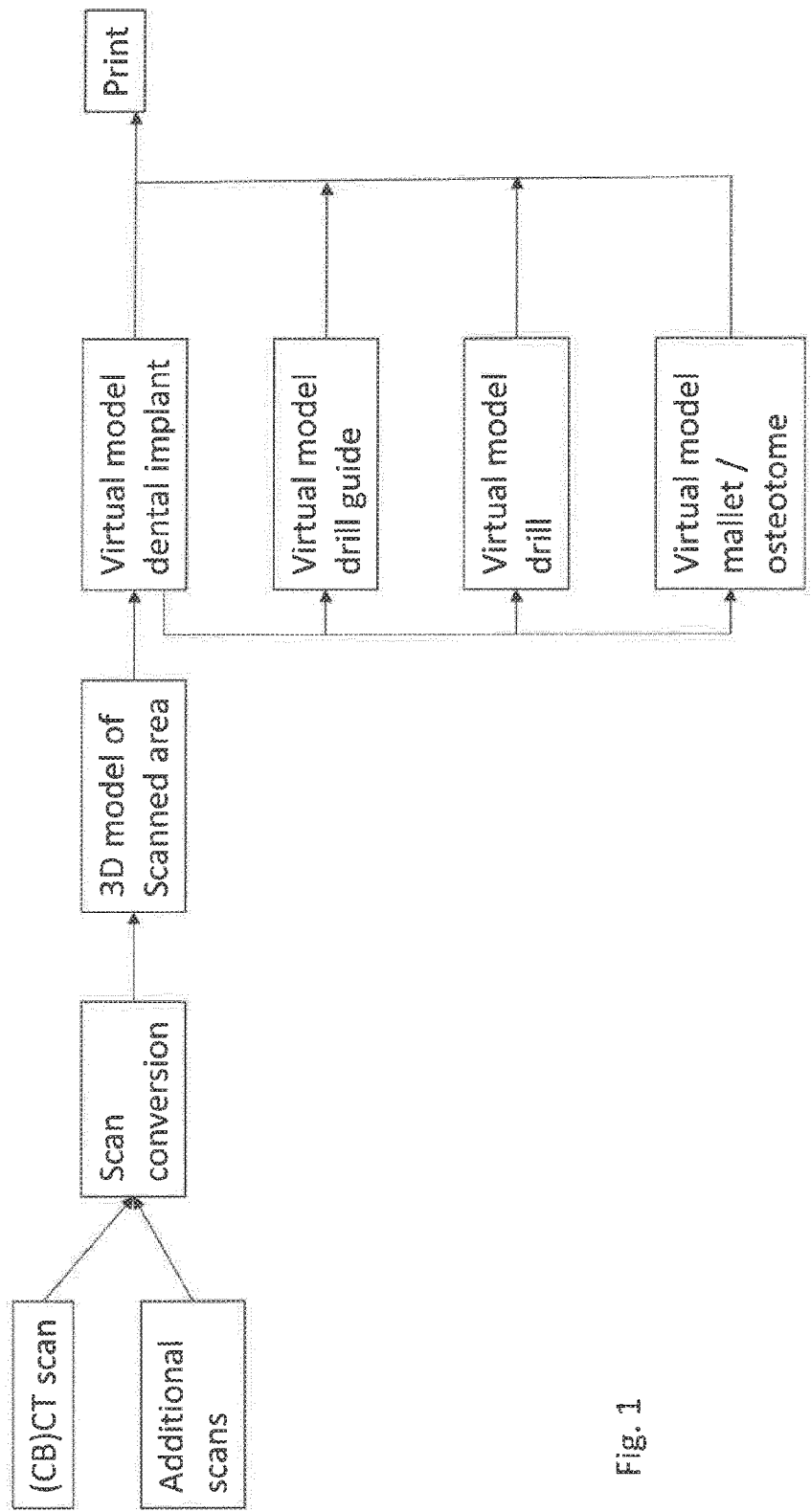
FIG. 1: shows a flow diagram representing the method according to the invention.

FIG. 1 shows a flow diagram showing consecutive steps of an exemplary embodiment of a method according to the invention.

After removal of a patients tooth the remaining dental alveolus is usually allowed to heal for some months to grow fresh jaw bone material. When the dental alveolus is sufficiently healed a CT scan is made. CT-scans typically show harder tissues, such as bone material and roots of adjacent teeth. Additionally, or alternatively, an MRI scan could be used to map the softer tissues, such as nerves. Optionally, an intraoral scan can be made to map the contours of the teeth and the soft tissues in the mouth, e.g., to optimize the fit of the drill guide on the soft tissues.

The CT scans and intraoral scans and/or other types of scans can be combined to form a single virtual model using software which is commonly known in the field. A suitable example of such software is the Simplant® software of Dentsply Implants, Sweden. Using different scan technologies may help to improve the accuracy of the virtual 3D model of the scanned area. For instance, (CB)CT scans may show some bias or distortion which can be compensated by a scan from a different source and type, so the overall accuracy of the virtual 3D model of the scanned area can be improved substantially. Ultra sound scanning can for example be used for modeling of the outline of hard bone tissue covered by gum. This can be combined with other scans, e.g., with MRI scans and/or intraoral scans which are typically more accurate with softer tissues. Suitable examples of software that can be used for this purpose include Digital Smile Design®, Dental Wings® and 3 Shape Exocad®.

The scans are converted into a virtual 3D model of the scanned area, typically in .skp, .dae, .3ds or some other suitable format. On basis of this virtual 3D model the optimum dimensions of the dental implant can be calculated. This results in a virtual model of the designed implant. The implant should have as much contact surface interfacing with adjacent bone material as the available space allows. The implant is individually designed to make optimal use of the available bone space, so it is typically cylindrical, conical or having a shape combining cylindrical and conical sections depending on the bone dimensions. The dental implant may also have an asymmetrical shape. In that case the toolings will also comprise one or more individualized osteotomes adapted to the individual asymmetric implant design.

The virtual model will be used with a 3D printer or similar rapid prototyping process. Therefore, the model will typically be in a .STL or a .OBJ format, to allow the printing software to read it. Computer programs for generating a virtual customized dental implant as a 3D print file on basis of CT scans are known in the art.

In a next step a virtual model is generated for a drilling guide on basis of the scan data and on basis of the virtual implant model. The drilling guide will have a lower surface resting on adjacent teeth, edentulous area covered by soft tissue, bone or an adjacent temporary implant. To avoid any movement of the guide during drilling, the supporting surface must accurately match the surfaces on which it rests. The drilling guide will comprise a drilling hole for guiding the drills to be used. This virtual model of the drilling guide will also be in a .STL or a .OBJ format or any other format suitable for processing with 3D printing software.

A further virtual model is generated of the toolings to be used, in particular the drills. Usually, a series of drills of increasing diameter will be used. The final drill will have a diameter which is typically about 0.4-0.6 mm less than the diameter of the dental implant matching the diameter of the dental implant, allowing the implant to be positioned in the drilled hole, e.g., by a self-tapping screw thread, and to make intimate contact with adjacent bone. Alternatively the osteotomy is shaped using osteotomes and the implant is tapped in place using a mallet.

In a next step, the dental implant, the drilling guide, and the drills and/or osteotomes are printed by communicating the respective virtual models to the printer. The same printer can be used for all components using the same printing material. If so desired, different printers and/or printing materials can be used.

Figure 2:
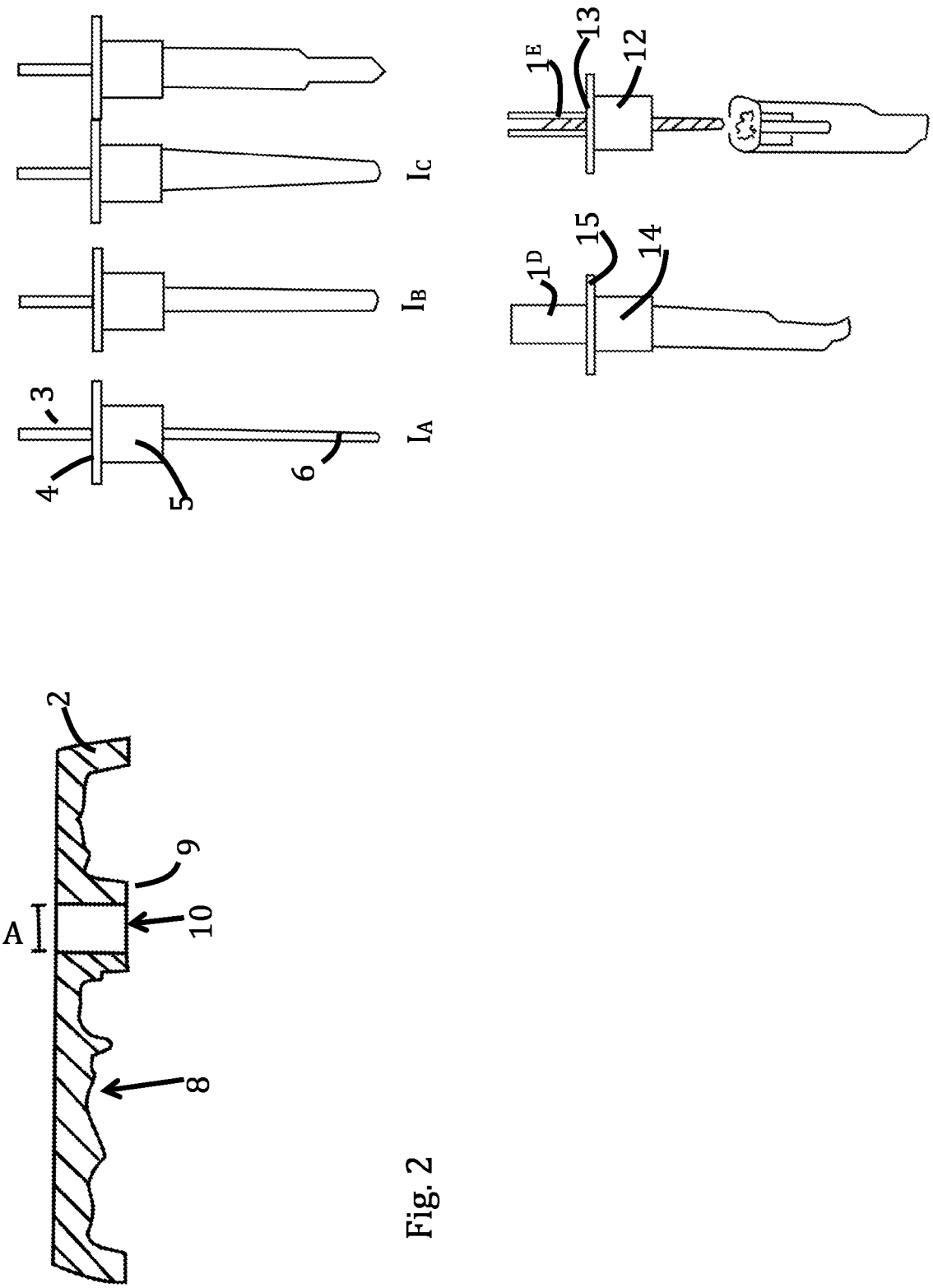
FIG. 2 shows a set of toolings according to the invention.

FIG. 2 shows a set of printed drills 1A, 1B, 1C, a drilling guide 2, a mallet 1D and an implant insertion device or driver 1E.

The set comprises three drills 1A, 1B, 1C of increasing diameter. Each of the three drills 1A, 1B, 1C comprise a top end 3, configured to engage a drill head of a drilling machine (not shown). Below the top end 3 the drills 1A, 1B, 1C comprise a stop 4 and a cylindrical guiding section 5. The guiding sections 5 of all drills 1A, 1B, 1C have the same diameter D and the same length L. Below the guiding sections 5 the drills 1A, 1B, 1C have the actual drill bodies 6 of increasing drilling diameter and of the specifically designed length.

The drilling guide 2 comprises a strip body 7 with a lower surface 8 having a surface structure exactly matching the geometry of adjacent dentures, so as to immobilize the drill guide 2 during drilling. At the position of the alveolus that is to be treated, the drill guide 2 comprises a cylindrical bus 9 resting on the jaw between the adjacent teeth. The cylindrical bus 9 is provided with a cylindrical guiding opening 10 with the same diameter D as the guiding sections 4. The guiding opening 10 is configured to receive the guiding sections 4 of the drill 1A, 1B, 1C in a sliding manner. This ensures that all three drills 1A, 1B, 1C can be positioned accurately and aligned in the very same direction in order to drill along essentially the same drilling axis. The axis of the guiding opening 10 may be vertical or may be inclined, depending on how the dental implant (not shown) should be positioned in the treated jaw bone.

The stop 4 at the top side of the guiding section 5, is wider than the diameter D. These stops 4 ensure that the dentist will not drill deeper than the required depth. In an alternative embodiment the guiding opening 10 of the drilling guide can be provided with a stop.

The resulting osteotomy is slightly smaller than implant in order to provide a narrow fit stabilizing the implant just after its positioning.

The implant can now be put in place, typically by means of an implant driver 1E. Such an implant driver 1E can be used to engage the individually designed and printed implant 11, e.g., with a conical click connection (not shown). The implant driver 1E can be provided with the same cylindrical guiding section 12 as the drills 1A, 1B, 1C, e.g., with an identical stop 13. The implant driver 1E can be sterilized after use for reuse. Due to the identical cylindrical shape and size of the guiding section 12 the implant 11 can be guided by means of the drilling guide 2. This way the implant exactly follows the osteotomy and it cannot be screwed or tapped any deeper than the prepared osteotomy.

Alternatively, the mallet 1D can be used to tap the implant 11 into the osteotomy. Like the implant driver 1E, the mallet is provided with an identical cylindrical guiding section 14 and an identical stop 15, so the implant can be tapped in exactly the right direction.

The method of the invention enables customized on-demand manufacture of the dental implant, the drilling guide and the drills and/or osteotomes to be used. Therefore, it is not necessary to use cylindrical or conical implants. Other implant shapes can also be used and the drilling guide can be designed to guide the drills or other osteotomy modelling devices to form drilling holes of a non-cylindrical outline.

The invention claimed is:

1. A method of customizing and manufacturing one or more customized toolings, wherein the toolings include at least one or more drills and/or one or more osteotomes for forming non-cylindrical holes, including at least one of a cutter, a chisel or a scraper, for preparing an osteotomy in a healed alveolus for receiving a dental implant, the method comprising the steps of:
   receiving scan data modeling a planned position of the osteotomy and surrounding jaw bone area before making the osteotomy;
   generating on the basis of the scan data a virtual implant model of the dental implant;
   generating a virtual tooling model using the virtual implant model, said virtual tooling model being a model of the one or more drills including at least the length, diameter, conical angle and pitch of each said drill, and/or of the one or more osteostomes on the basis of the virtual implant model; and
   computer aided manufacturing of the one or more customized toolings on the basis of the virtual tooling model.

2. The method according to claim 1 wherein the dental implant is made by a computer aided manufacturing process on the basis of said virtual implant model.

3. The method according to claim 1, wherein the one or more customized toolings is one or more osteotomes manufactured by a rapid prototyping process.

4. The method according to claim 3, wherein the rapid prototyping process includes 3D printing, stereolithography, fused deposition modeling, laminated object modeling, selective laser sintering, or computer aided milling.

5. The method according to claim 4, wherein the one or more customized osteotomes is formed of the same or different material as the dental implants.

6. The method according to claim 5, wherein the one or more customized osteotomes are formed of a printable composition comprising titanium or zirconium.

7. The method according to claim 4, wherein the toolings include one or more drills manufactured by the rapid prototyping process.

8. The method according to claim 4, wherein the scan data are obtained by computed tomography (CT) scanning.

9. The method according to claim 8, wherein the CT-scan is combined with additional scans.

10. The method according to claim 9, wherein the additional scans are selected from a magnetic resonance imaging scan and an intraoral scan.

11. A method for preparing an implantation of a dental implant, wherein one or more customized osteotomes are manufactured according to the method according to claim 8.

12. The method according to claim 11, wherein the toolings further include at least one drill comprising a guiding section and a drilling guide comprising a guiding opening configured to receive the guiding section of the drill in a sliding manner.

13. The method according to claim 12, wherein the toolings include a series of drills of increasing diameter, all provided with a guiding section of the same dimensions.

14. The method according to claim 12, wherein the guiding section comprises a stop.

15. The method according to claim 12, wherein at least one customized dental implant is employed.

16. The method according to claim 1, wherein the osteotomes include two or more of scrapers, cutters and chisels.

\* \* \* \* \*